US00PP31301P2

(12) United States Plant Patent
Hansen

(10) Patent No.: US PP31,301 P2
(45) Date of Patent: Dec. 31, 2019

(54) ***VERONICA* PLANT NAMED 'PURPLE ILLUSION'**

(50) Latin Name: ***Veronica spicata* L.**
Varietal Denomination: Purple Illusion

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 16/501,206

(22) Filed: Mar. 6, 2019

(51) Int. Cl.
*A01H 5/02* (2018.01)
*A01H 6/68* (2018.01)

(52) U.S. Cl.
USPC ..... Plt./251

(58) Field of Classification Search
USPC ..... Plt./251
CPC ..... A01H 5/02; A01H 6/68
See application file for complete search history.

*Primary Examiner* — Annette H Para

(57) ABSTRACT

The new and distinct cultivar of ornamental spike speedwell plant, *Veronica spicata* 'Purple Illusion', with short habit, stiff, upright, branched, dense spikes rosy-purple flowers beginning in late spring and continuing for up to five weeks above deep green foliage. The new plant is useful in the landscape as a specimen, en masse, as a container plant or as a cut flower.

1 Drawing Sheet

Botanical classification: *Veronica spicata* L.;
Variety denomination: 'Purple Illusion';

STATEMENT REGARDING PRIOR DISCLOSURES UNDER 37 CFR 1.77(b)(6)

The first public disclosure of the claimed plant, in the form of a photograph and brief description on a website operated by Walters Gardens, Inc. on Dec. 1, 2018. Prior to that the claimed plant was first sold privately on Mar. 26, 2018 by Walters Gardens, Inc., who obtained the plant and all information relating thereto, from the inventor. No plants of *Veronica* 'Purple Illusion' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of spike speedwell, botanically known as *Veronica spicata* 'Purple Illusion', and hereinafter referred to as the cultivar 'Purple Illusion' or the "new plant". The new plant was cross by the inventor on Jun. 29, 2012 in the hybridizing greenhouses of a wholesale perennial nursery in Zeeland, Mich., USA. The female or seed parent was a proprietary unreleased hybrid known only by the breeder code 08-57-03 (not patented) and the male or pollen parent was 'Enchanted Indigo' U.S. Plant Pat. No. 26,603.

The new plant was assigned the breeder code of 12-30-4. 'Purple Illusion' has been asexually propagated initially division and later by basal cuttings and shoot tip tissue culture at the same nursery in the greenhouses in Zeeland, Mich., since the summer of 2014 with subsequent asexually propagated plants found to be identical to the original selection with all the same traits as the original seedling.

BRIEF SUMMARY OF THE PLANT

*Veronica* 'Purple Illusion' is unique from all other spike speedwell known to the inventor. Several other cultivars may have some similar traits, but this is the only variety known by the inventor to have the following characteristic combinations that establish the new plant as unique:

1. Compact short habit with stiff, upright spikes above dense stems of deep green foliage.
2. Scapes with numerous, dense flowers of rosy-purple petals.
3. Branched peduncles begin blooming in late spring and continue for at least five weeks into summer.

The closest comparison varieties known to the inventor are 'Mona Lisa Smile' U.S. Plant Pat. No. 30,477, 'Purpleicious' U.S. Plant Pat. No. 17,639, 'Hocus Pocus' U.S. Plant Pat. No. 23,853 and 'Purple Explosion' U.S. Plant Pat. No. 24,757. 'Mona Lisa Smile' is taller in habit and has a flower color that is a lighter rosy purple. 'Purpleicious' has flowers that are lighter violet-purple and the habit is taller. 'Purple Explosion' has flowers that are deep purple-pink on plants that are much taller than the new plant. 'Hocus Pocus' has similar habit and size, but the flowers are a vivid violet-purple, and flower induction does not require vernalization. The female parent, 08-57-03, is taller and the flower was a lighter shade of lavender purple. The male parent has darker royal purple flowers with a tighter habit.

BRIEF DESCRIPTION OF THE DRAWINGS

The photographs of the new plant demonstrate the overall appearance and unique traits of 'Purple Illusion' as a three-year-old plant grown in a full-sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
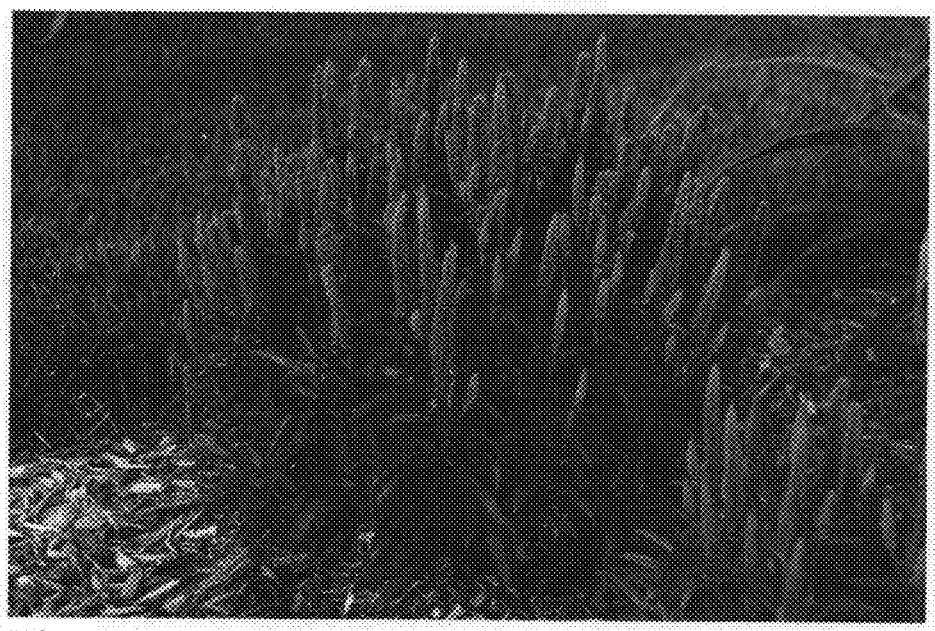
FIG. 1 shows the habit of the new plant in full flower.
Figure 2:
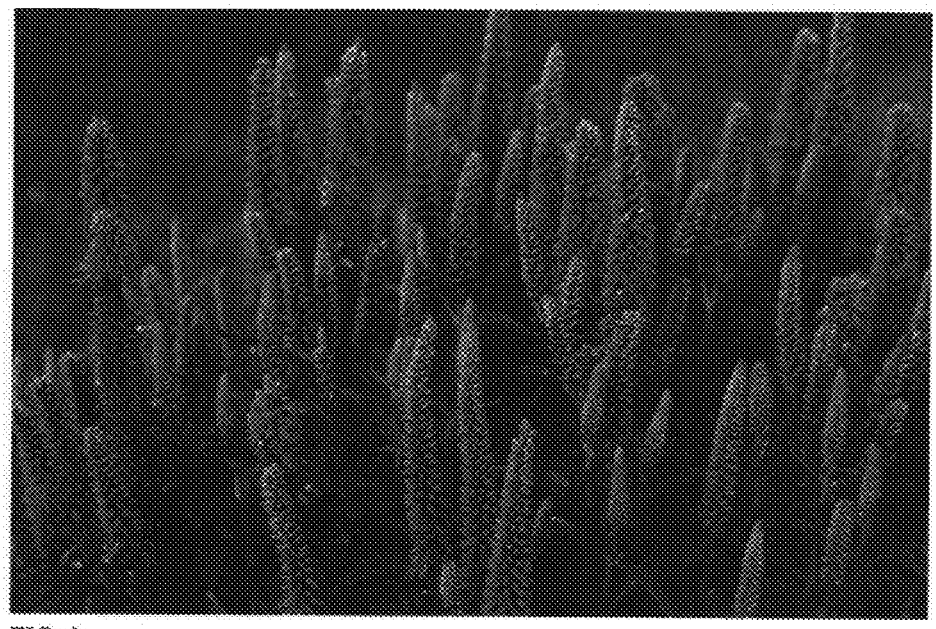
FIG. 2 shows a close-up of the flowers and buds.

The following descriptions and color references of *Veronica* 'Purple Illusion' are based on the 2015 edition of The Royal Horticultural Society Colour Chart except where common dictionary terms are used. 'Purple Illusion' has not been observed under all possible environments. The phenotype may vary slightly with different growing environments such as temperature, light, fertility, soil pH, moisture and maturity levels, but without any change in the genotype. The following observations and size descriptions are based on three-year-old grown in a full-sun trial garden and one-year-old plants grown in a partially shaded greenhouse of a nursery in Zeeland, Mich.

Botanical classification: *Veronica spicata;*

Parentage: The female (seed parent) is 08-57-03, a selection of open-pollinated 'Purpleicious'; the male or pollen parent was 'Enchanted Indigo';

Propagation: The plant roots from cuttings in about 2 weeks and finishes to flowering in a 3.8 liter container in 8 to 10 weeks following a vernalization period of about 8 weeks;

Roots: Fibrous; heavily branching; color between RHS 164C and RHS 164D;

Plant habit: Hardy herbaceous perennial, compact, with about 48 stems; main stems branching in distal portion; to about 45 cm tall and clumping to about 45 cm wide; flowering beginning late spring in Michigan and continuing for up to 5 weeks;

Leaves: Simple; flat; lanceolate; opposite; margin ciliolate, serrated with about 5.5 teeth per centimeter; micro-puberulent adaxial and glabrous between veins abaxial, lustrous adaxial and matte abaxial; acute apex; distal leaves with attenuate base and proximal leaves with rounded base; about 7.5 cm long by 27.0 mm wide near middle, average about 6.5 cm long and 25.0 mm wide, decreasing in both length and width distally; about 16 leaves per stem;

Leaf color: Mature adaxial between RHS 139A and RHS NN137A, abaxial nearest RHS 137A; young expanding adaxial nearest RHS 144A, abaxial nearest RHS 144A;

Veins: Pinnate, abaxial midrib costate; puberulent abaxial and glabrate to glabrous adaxial;

Vein color: Adaxial midrib and proximal lateral veins nearest RHS 145A and distal lateral veins nearest RHS 146D; abaxial midrib nearest RHS 146D and lateral veins nearest RHS 144A;

Petiole: Simple, puberulent abaxial and glabrous adaxial; margin ciliolate; base slightly clasping; to about 12.0 mm long and 3.0 mm wide decreasing distally to an average about 4.0 mm long and 2.5 mm wide;

Petiole color: Adaxial nearest RHS 138B; abaxial nearest RHS 145A;

Stem: Cylindrical; puberulent; length about 20.0 cm before flowers, diameter about 3.0 mm at base; color nearest RHS 138A;

Internodes: 9 below flowers; average about 2.2 cm apart; node color nearest RHS 138A;

Inflorescence: Lightly branched upright spikes in compressed conglomerate; about 12 cm long and 4.5 cm wide with two lateral branches; with about 250 flowers per center stem, 75 flowers per branch and about 400 per branched peduncle;

Flower bud one to two days prior to opening: Convolute; oblong; rounded base and apex; glabrous; about 5.0 mm long and 2.0 mm diameter;

Flower bud color one to two days prior to opening: Nearest RHS 83C with basal 1.0 mm lighter than RHS 145D;

Flowers: Zygomorphic, perfect, complete; about 6.0 mm wide and about 11.0 mm long to exserted anthers; corolla about 6.0 mm across and about 6.0 mm long; corolla tube fused in basal 2.5 mm and 2.0 mm diameter near base; flowers persist individually for 4 to 6 days whether on the plant or cut; petals self-cleaning, sepals and style persistent; attitude outwardly;

Flower fragrance: Not detectible;

Flower timing: Late spring and continuing for about five weeks;

Petals: Four; one slightly larger petal above, two on either side, one slightly smaller below; rounded apices; entire; glabrous adaxial and abaxial except basal 2.0 mm adaxial of fused tube with pubescent tuft; fused in basal 2.5 mm; larger top and side petals about 6.0 mm long by 4.0 mm wide, smaller lower petal about 6.0 mm long and 3.5 mm wide;

Petal color: Abaxial and adaxial nearest RHS 83C with corolla tube base lightening RHS NN155D with proximal 0.5 mm nearest RHS 145D; adaxial tuft of hairs nearest RHS NN155D;

Androecium:

*Filaments.*—Two; divergent; glabrous; epipetalous about 1.0 mm from base; about 8.5 mm long by 0.3 mm; color nearest RHS N82B distally becoming white, RHS NN155D proximally.

*Anther.*—Dorsifixed, longitudinal; ellipsoidal; with acute rounded becoming acute, base rounded; about 2.0 mm long and 1.0 mm wide; ventral color nearest RHS N77B and dorsal nearest RHS N81B, nearest RHS 202A abaxial after pollen dehiscence.

*Pollen.*—Abundant, globose, less than 0.1 mm; nearest RHS 10C.

Gynoecium: One, superior; exserted; persists after petal drop;

*Style.*—Cylindrical; straight; attitude outwardly to slightly drooping; about 8.0 mm long by 0.5 mm; color between RHS N81C and RHS N81B.

*Stigma.*—Globose; about 0.3 mm in diameter; color RHS 76B.

*Ovary.*—Globose to ellipsoid; about 1.2 mm long and 1.0 mm across; color nearest RHS 146D.

Calyx: Campanulate; 3.0 mm long and 3.0 mm diameter;

Sepals: Four; two larger and two smaller; lanceolate; adaxial dull, glabrous; abaxial microscopically puberulent; acute apex; basal 1.5 mm fused forming campanulate calyx; margin entire, ciliolate; larger pair about 3.0 mm long and 1.0 mm wide; smaller pair about 2.5 mm long and 1.0 mm wide;

Sepal color: Abaxial and adaxial nearest RHS 138A;

Peduncle: About 70 per plant; raceme, strong, virgate, branched at upper nodes; cylindrical; pubescent distally to glabrescent proximally; flowering portion to about 12.0 cm long, about 4.5 cm across and diameter about 2.0 mm below flowers;

Peduncle color: Nearest RHS 138A;

Pedicel: Rigid; cylindrical, puberulent; about 0.5 mm long and 0.5 mm wide, attitude semi-upright;

Pedicel color: Nearest RHS 138B;

Bract: One; subtending each flower; linear; narrowly acute apex; entire; sessile attenuate base; proximal bracts about 1.0 cm long and 2.0 mm wide and decreasing distally to about 3.0 mm long and less than 1.0 mm wide;

Bract color: Nearest RHS 137A adaxial and nearest RHS 137B abaxial;

Fruit: Ellipsoid with rounded apex and base, about 2.5 mm long and 2.0 mm across; color between RHS 165A and RHS 165B;

Hardiness, pest and disease resistance: The new plant grows best with plenty of moisture and adequate drainage, but is able to tolerate some drought when mature. Hardiness at least from USDA zone 4 through 8. Disease and pest resistance beyond what is typical of that of other spike speedwell has not been observed.

I claim:

1. A new and distinct cultivar of ornamental Spike Speedwell plant, *Veronica spicata* 'Purple Illusion', as herein described and illustrated.

* * * * *